US012742761B2

(12) United States Patent
Imigi et al.

(10) Patent No.: US 12,742,761 B2
(45) Date of Patent: Sep. 22, 2026

(54) GAS LEAKAGE DETECTION APPARATUS, GAS LEAKAGE DETECTION SYSTEM, GAS LEAKAGE DETECTION METHOD, AND NON-TRANSITORY COMPUTER READABLE MEDIUM

(71) Applicant: Asahi Kasei Microdevices Corporation, Tokyo (JP)

(72) Inventors: Ayano Imigi, Tokyo (JP); Keiichiro Kuwata, Tokyo (JP); Takaaki Furuya, Tokyo (JP)

(73) Assignee: Asahi Kasei Microdevices Corporation, Tokyo (JP)

( * ) Notice: Subject to any disclaimer, the term of this patent is extended or adjusted under 35 U.S.C. 154(b) by 0 days.

(21) Appl. No.: 18/953,087

(22) Filed: Nov. 20, 2024

(65) Prior Publication Data

US 2025/0172530 A1 May 29, 2025

(30) Foreign Application Priority Data

Nov. 24, 2023 (JP) ................................ 2023-198767
Oct. 3, 2024 (JP) ................................ 2024-174073

(51) Int. Cl.
*G01N 33/00* (2006.01)
*B64C 39/02* (2023.01)
*G01M 3/04* (2006.01)

(52) U.S. Cl.
CPC ......... *G01N 33/0063* (2013.01); *B64C 39/02* (2013.01); *G01M 3/04* (2013.01); *G01N 33/0006* (2013.01)

(58) Field of Classification Search
CPC . G01N 33/0063; G01N 33/0006; G01M 3/04; B64C 39/02
See application file for complete search history.

(56) References Cited

U.S. PATENT DOCUMENTS 3,864,628 A * 2/1975 Klass .................. G01N 33/005 73/31.06
9,494,511 B2 * 11/2016 Wilkins ................ G01J 3/0264
10,520,387 B2 12/2019 Wang
10,677,771 B2 * 6/2020 Dittberner ................ G08G 5/55
(Continued)

FOREIGN PATENT DOCUMENTS

EP 4481353 A1 12/2024
JP H1172411 A 3/1999
(Continued)

*Primary Examiner* — John A Tweel, Jr.

(57) ABSTRACT

A gas leakage detection apparatus may include a movement control unit that controls a movement of a moving object on which a gas sensor is mounted. The gas leakage detection apparatus may include an acquisition unit that acquires a measurement result of target gas that is obtained by a measurement by the gas sensor while the moving object is moving over a target area, and a response time from a start of a measurement of the gas sensor until an output of the measurement result. The gas leakage detection apparatus may include a detection unit that detects a leakage of the target gas in the target area based on the measurement result and the response time. The detection unit may detect the leakage of the target gas in the target area based on the measurement result and location information of the moving object, to identify a gas leakage spot.

17 Claims, 9 Drawing Sheets

(56) References Cited

U.S. PATENT DOCUMENTS

| | | | | |
|---|---|---|---|---|
| 12,346,132 | B2 * | 7/2025 | Al-Qahtani | G05D 1/46 |
| 2018/0222581 | A1 | 8/2018 | Nagasawa | |
| 2021/0380272 | A1 * | 12/2021 | Parrott | B64U 10/25 |
| 2023/0213413 | A1 * | 7/2023 | Mohr, Jr. | G01N 33/0073<br>73/31.01 |
| 2025/0003793 | A1 | 1/2025 | Tomomichi | |

FOREIGN PATENT DOCUMENTS

| | | | |
|---|---|---|---|
| JP | 2016080629 | A | 5/2016 |
| JP | 2023045315 | A | 4/2023 |
| JP | 2023117217 | A | 8/2023 |
| JP | 7336621 | B1 | 9/2023 |

* cited by examiner

GAS LEAKAGE DETECTION APPARATUS, GAS LEAKAGE DETECTION SYSTEM, GAS LEAKAGE DETECTION METHOD, AND NON-TRANSITORY COMPUTER READABLE MEDIUM

The contents of the following patent application(s) are incorporated herein by reference:

NO. 2023-198767 filed in JP on Nov. 24, 2023

NO. 2024-174073 filed in JP on Oct. 3, 2024.

BACKGROUND

1. Technical Field

The present invention relates to a gas leakage detection apparatus, a gas leakage detection system, a gas leakage detection method, and a non-transitory computer readable medium.

2. Related Art

Patent document 1 describes a gas leakage detection method for detecting a gas leakage by performing a gas analysis operation at a timing at which a mobile detection apparatus becomes a static state.

Prior Art Documents

Patent Document

Patent Document 1: U.S. Pat. No. 10,520,387 specification

DESCRIPTION OF EXEMPLARY EMBODIMENTS

The present invention will be described below through embodiments of the invention, but the following embodiments do not limit the invention according to the claims. In addition, not all of the combinations of features described in the embodiments are essential to the solutions of the invention.

Figure 1:
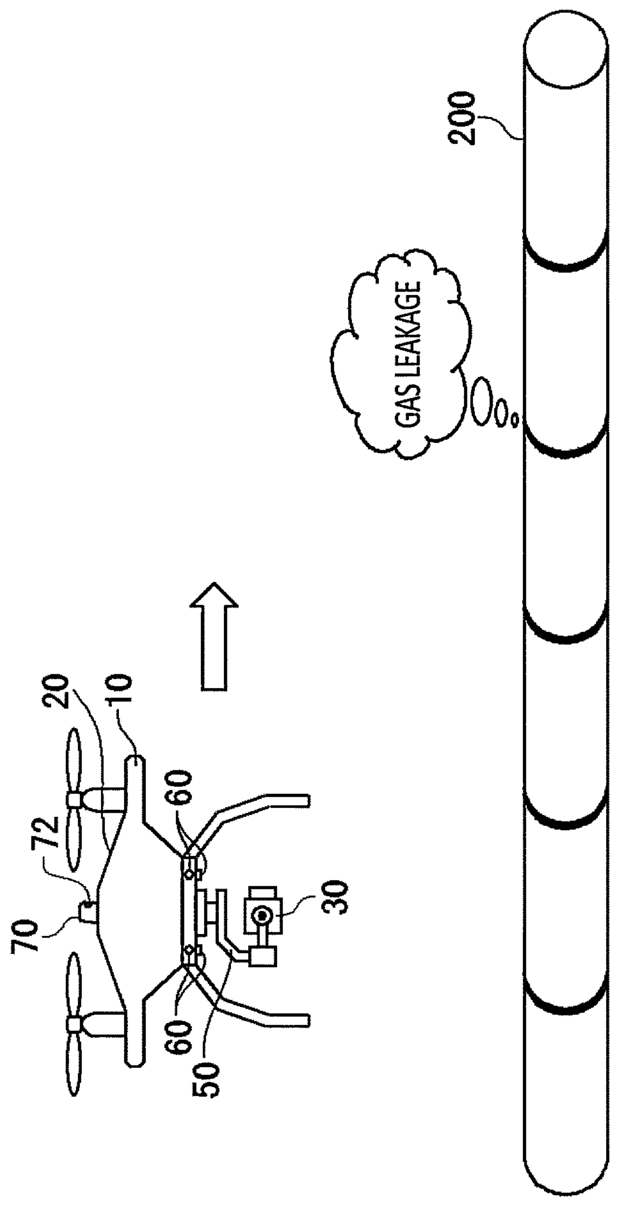
FIG. 1 shows an example of an overall configuration of a gas leakage detection system according to the present embodiment.
Figure 1:
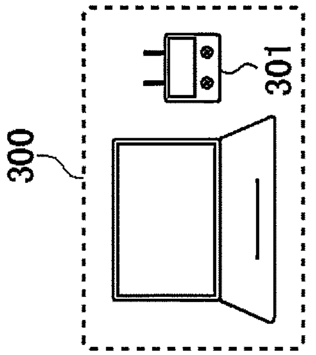

FIG. 1 shows an example of an overall configuration of a gas leakage detection system according to the present embodiment. The gas leakage detection system includes an Unmanned Aerial Vehicle (UAV) 10 and a remote operation apparatus 300.

The UAV 10 includes a UAV body 20, a gimbal 50, a plurality of image capturing apparatuses 60, an image capturing apparatus 30, and a gas sensor 70. The UAV 10 is an example of a moving object. The moving object is a concept that includes a flying object moving in the air, a vehicle moving on the ground, a ship moving on water, or the like. The flying object moving in the air is a concept including the UAV, and another aircraft, airship, helicopter, and the like moving in the air.

The UAV body 20 includes a plurality of rotary wings. The plurality of rotary wings are an example of a propelling unit. The UAV body 20 makes the UAV 10 fly by controlling the rotation of the plurality of rotary wings. The UAV body 20 makes the UAV 10 fly by using four rotary wings, for example. The number of the rotary wings is not limited to four. In addition, the UAV 10 may be a fixed-wing aircraft without the rotary wings.

The gas sensor 70 detects the gas concentration of to-be-measured gas. The gas sensor 70 may be an optical gas sensor. The optical gas sensor may be an NDIR (Non Dispersive Infrared) gas sensor. In addition, a measurement principle of the gas sensor 70 may be Tunable Diode Laser Absorption Spectroscopy (TDLAS), DIAL (Differential Absorption LiDAR), TCSPC (Time Correlated Single Photon Counting), a photoacoustic method, a semiconductor method, a solid electrolyte method, a thermal conduction method, an acoustic wave method, an optical gas imaging method, or a capacitance method.

The gas sensor 70 may include a statistical processing unit which performs a statistical process on the measurement result. The statistical process may mean generating statistical information including at least one of an average value, a maximum value, a minimum value, a distribution, a moment, or a histogram from the measurement result.

The to-be-measured gas may be combustible gas such as methane, propane, ethanol, hydrogen, ethylene, and MCH (Methylcyclohexane). The to-be-measured gas may be toxic gas such as carbon monoxide, hydrogen sulfide, formaldehyde, and ammonia. The to-be-measured gas may be greenhouse gas such as carbon dioxide, nitrous oxide, and refrigerant gas.

The gas sensor 70 may be provided on the top surface of the UAV body 20. The gas sensor 70 has an intake 72 into which the gas is taken. The intake 72 may be provided on the top surface of the UAV body 20 such that the intake 72 faces the front side in a case in which the UAV 10 moves forward. If the UAV 10 measures the gas concentration of the to-be-measured gas while moving upward, the intake 72 may be provided on the top surface of the UAV body 20 such that the intake 72 faces the top side in a case in which the UAV 10 moves upward. The gas sensor 70 may have a driving mechanism that changes the posture with respect to the UAV body 20 such that the orientation of the intake 72 of the gas sensor 70 changes corresponding to the movement direction of the UAV 10. The gas sensor 70 may have a plurality of intakes oriented to different directions, and may have a switching mechanism that switches an intake for taking the to-be-measured gas thereto among the plurality of intakes corresponding to the movement direction of the UAV 10. The intake of the gas sensor 70 may be an intake with a hemispherical shape such that the gas can be taken in from a plurality of directions.

The UAV 10 may have an arm for providing the gas sensor 70, which extends from the UAV body 20, and the gas sensor 70 may be provided on a tip of the arm.

When a moving object on which the gas sensor 70 is mounted uses an internal combustion engine as a drive source, the intake of the gas sensor 70 may be provided at a position that is separated from a vent for exhausting exhaust gas of the internal combustion engine. If the vent is provided on the rear side of the moving object, the intake of the gas sensor 70 may be provided on the front side of the moving object. The drive source of the moving object on which the gas sensor 70 is mounted may be a motor. For the motor, because exhaust gas is not generated from the drive source, the gas concentration can be accurately measured without inhibiting the operation of the gas sensor, and consequently, the measurement can be performed in a short time.

The image capturing apparatus 30 captures an object included in a desired imaging range. The gimbal 50 rotatably supports the image capturing apparatus 30. The gimbal 50 is an example of the support mechanism. The gimbal 50 may change the posture of the image capturing apparatus 30 by rotating the image capturing apparatus 30 around at least one of a yaw shaft, a pitch shaft, and a roll shaft.

The plurality of image capturing apparatuses 60 is a sensing camera for capturing the surroundings of the UAV 10 for controlling the flight of the UAV 10. Two image capturing apparatuses 60 may be provided on a front surface that is the nose of the UAV 10. Still another two image capturing apparatuses 60 may be provided on a bottom surface of the UAV 10. The two image capturing apparatuses 60 on the front side becomes a pair, and may function as a so-called stereo camera. The two image capturing apparatuses 60 on a side of the bottom surface also consists a pair, and may function as a stereo camera. The image capturing apparatus 60 may measure the existence of an object included in the imaging range of the image capturing apparatus 60, and a distance to the object. The image capturing apparatus 60 is an example of a measurement apparatus that measures an object existing in an image-capturing direction of the image capturing apparatus 30. The measurement apparatus may be another sensor such as an infrared sensor, or an ultrasonic sensor that measures an object existing in the image-capturing direction of the image capturing apparatus 30. Three-dimensional space data of the surroundings of the UAV 10 may be generated based on the image captured by the plurality of image capturing apparatuses 60. The number of the image capturing apparatuses 60 included in the UAV 10 is not limited to four. There is no problem as long as the UAV 10 includes at least one image capturing apparatus 60. The UAV 10 may include at least one image capturing apparatus 60 for each of the nose, the tail, the side surface, the bottom surface, and the top surface of the UAV 10. An angle of view that can be set in the image capturing apparatus 60 may be wider than an angle of view that can be set in the image capturing apparatus 30. The image capturing apparatus 60 may have a single focal lens or a fisheye lens. The image capturing apparatus 30 may be an infrared camera. The image capturing apparatus 60 may be an infrared camera.

The remote operation apparatus 300 communicates with the UAV 10 and remotely operates the UAV 10. The remote operation apparatus 300 may communicate with the UAV 10 in a wireless manner. The remote operation apparatus 300 transmits indication information indicating, to the UAV 10, various instructions that relate to the movement of the UAV 10 such as moving upward, moving downward, acceleration, deceleration, moving forward, moving backward, and pivoting. The indication information includes indication information for raising the altitude of the UAV 10, for example. The indication information may indicate an altitude at which the UAV 10 should be positioned. The UAV 10 moves so as to be positioned at the altitude indicated by the indication information received from the remote operation apparatus 300. The indication information may include a rise instruction for raising the UAV 10. The UAV 10 moves upward while receiving the rise instruction. The remote operation apparatus 300 is an example of a gas leakage detection apparatus that detects a gas leakage in a target area in a facility of production/transportation/storage/consumption of gas that is a target of gas detection, based on the measurement result from the gas sensor 70. The facility of production/transportation/storage/consumption of gas may be a natural gas mine or a pipeline 200, for example.

The remote operation apparatus 300 may control the movement of the UAV 10 such that the UAV 10 moves according to a predetermined movement route over the target area. The remote operation apparatus 300 may control the flight of the UAV 10 such that the UAV 10 flies at a predetermined altitude according to a predetermined flight route over the target area. The remote operation apparatus 300 may control the flight of the UAV 10 so as to move upward or move downward in each of a plurality of measurement spots in the target area. The remote operation apparatus 300 may control the flight of the UAV 10 so as to move upward or move downward while pivoting in each of the plurality of measurement spots in the target area.

According to the gas leakage detection system configured in this manner, the UAV 10 detects the gas concentration of the to-be-measured gas with the gas sensor 70 while moving over the target area that is the target of gas detection such as the pipeline 200, and the remote operation apparatus 300 detects the gas leakage of the target area based on the gas concentration that is measured with the gas sensor 70. In this manner, the time until the inspection of the gas leakage in the entire region to be detected is completed can be reduced.

Note that, in the present embodiment, an example is described, in which the remote operation apparatus 300 functions as the control apparatus that controls a gas leakage detection apparatus, the gas concentration measurement apparatus that measures the concentration of gas, or the UAV 10. However, the UAV 10 may function as the gas leakage detection apparatus. Alternatively, an apparatus that can communicate with a UAV 10 other than the UAV 10 and the remote operation apparatus 300 may function as the gas leakage detection apparatus.

Figure 2:
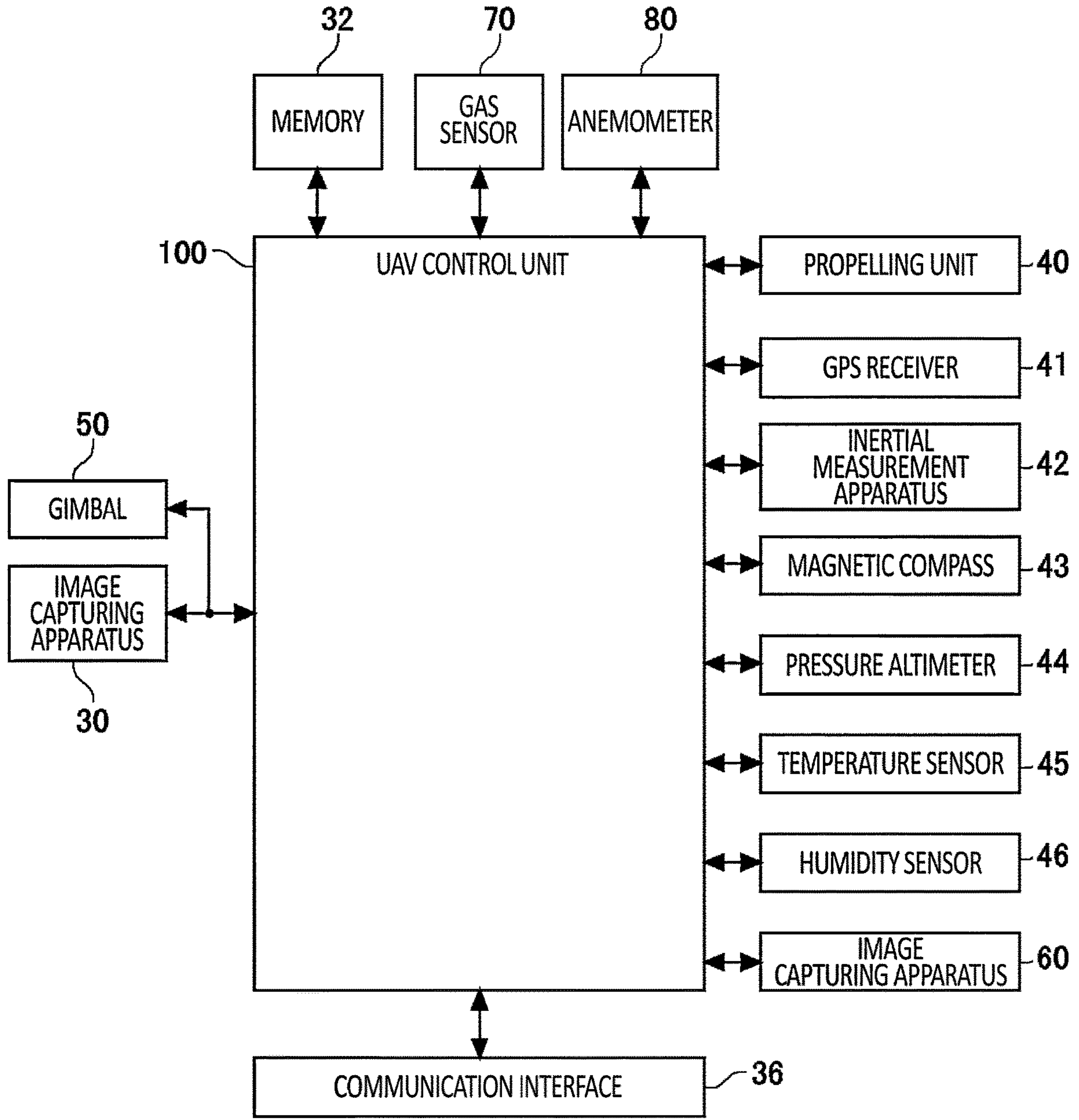
FIG. 2 shows an example of a functional block of an Unmanned Aerial Vehicle (UAV).

FIG. 2 shows an example of a functional block of the UAV 10. The UAV 10 includes a UAV control unit 100, a memory 32, a communication interface 36, a propelling unit 40, a GPS receiver 41, an inertial measurement apparatus 42, a magnetic compass 43, a pressure altimeter 44, a temperature sensor 45, a humidity sensor 46, a gimbal 50, an image capturing apparatus 60, an image capturing apparatus 30, a gas sensor 70, and an anemometer 80.

The communication interface 36 communicates with another apparatus such as the remote operation apparatus 300. The communication interface 36 may receive indication information including various instructions for the UAV control unit 100 from the remote operation apparatus 300. The memory 32 stores a program and the like required by the UAV control unit 100 for controlling the propelling unit 40, the GPS receiver 41, the inertial measurement apparatus (IMU) 42, the magnetic compass 43, the pressure altimeter 44, the temperature sensor 45, the humidity sensor 46, the gimbal 50, the image capturing apparatus 60, the image capturing apparatus 30, the gas sensor 70, and the anemometer 80. The memory 32 may be a computer-readable recording medium, and may include at least one of an SRAM, a DRAM, an EPROM, an EEPROM (registered trademark), and a flash memory such as a USB memory. The memory 32 may be provided inside the UAV body 20. The memory 32 may be provided removably from the UAV body 20.

The UAV control unit 100 controls, according to the program stored in the memory 32, the flight, the capture, and the measurement performed by various types of sensors, of the UAV 10. The UAV control unit 100 may be configured by a microprocessor such as a CPU or an MPU, a microcontroller such as an MCU, and the like. The UAV control unit 100 controls the flight, the capture, and the measurement of the UAV 10 according to the instruction received from the remote operation apparatus 300 via the communication interface 36.

The propelling unit 40 propels the UAV 10. The propelling unit 40 has a plurality of rotary wings and a plurality of drive motors that rotate the plurality of rotary wings. The propelling unit 40 rotates the plurality of rotary wings via the plurality of drive motors according to the instruction from the UAV control unit 100, to make the UAV 10 fly.

The GPS receiver 41 receives a plurality of signals indicating the time that is emitted from a plurality of GPS satellites. The GPS receiver 41 calculates the position (latitude and longitude) of the GPS receiver 41, that is, the position (latitude and longitude) of the UAV 10, based on the plurality of signals that are received. In addition, to calculate the position of the UAV 10, an RTK (REAL TIME KINEMATIC) or an SLAM (SIMULATANEOUS LOCALIZATION AND MAPPING) may be used. When the RTK is used to calculate the position, a base station may be arranged in a facility of production/transportation/storage/consumption of gas that is a target of calculation. The IMU 42 detects the posture of the UAV 10. The IMU 42 detects, as the posture of the UAV 10, accelerations in three axial directions of front and rear, left and right, and top and bottom of the UAV 10, and angular velocity in three axial directions of pitch, roll, and yaw. The magnetic compass 43 detects the orientation of the nose of the UAV 10. The pressure altimeter 44 detects the altitude at which the UAV 10 flies. The pressure altimeter 44 detects the air pressure in the surroundings of the UAV 10, converts the detected air pressure into the altitude, and detects the altitude. The temperature sensor 45 detects the temperature in the surroundings of the UAV 10. The humidity sensor 46 detects the humidity in the surroundings of the UAV 10.

The gas sensor 70 may be an NDIR gas sensor that detects the gas concentration of to-be-measured gas. The anemometer 80 measures the wind direction with respect to the UAV 10, and the wind speed.

Figure 3:
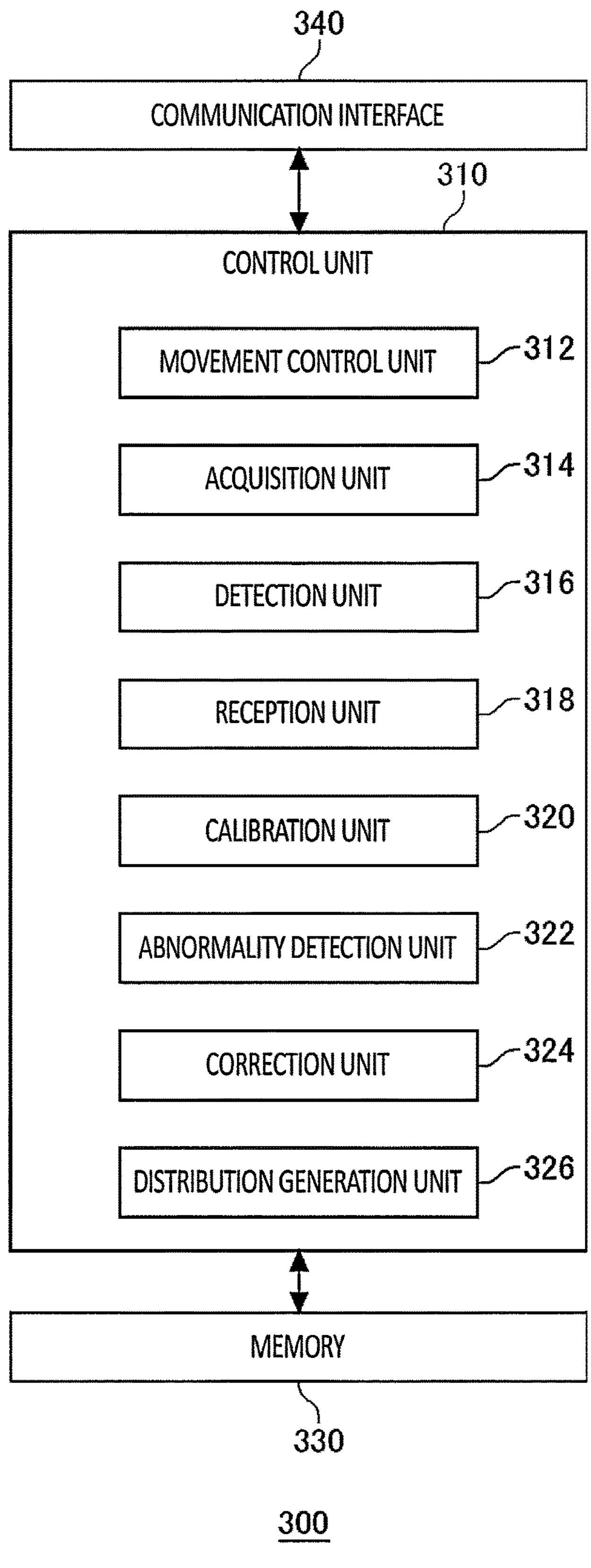
FIG. 3 shows an example of a functional block of a gas leakage detection apparatus.

FIG. 3 is a functional block diagram of the remote operation apparatus 300. The remote operation apparatus 300 may include a computer having a central processing unit (CPU) and memory. The remote operation apparatus 300 may include a transmitter 301 that transmits, to the UAV 10, a control instruction for controlling the flight of the UAV 10 corresponding to the operation of the user.

The computer may be a computer such as a personal computer, a tablet computer, a smartphone, a workstation, a server computer, or a general purpose computer, or may be a computer system in which a plurality of computers is connected to each other. Such a computer system is also a computer in a broad sense. The computer may be a special-purpose computer that is designed for controlling the UAV 10, or may be a special-purpose hardware that is implemented by a dedicated circuit. The computer may be implemented by a virtual computer environment. When the computer is used, the remote operation apparatus 300 is implemented by performing a program by the computer.

The remote operation apparatus 300 includes a control unit 310, a memory 330, and a communication interface 340. The remote operation apparatus 300 functions as a gas leakage detection apparatus. The control unit 310 may be implemented by a CPU. The memory 330 stores various programs related to a movement control of the UAV 10 and the gas leakage detection control performed by the remote operation apparatus 300.

The control unit 310 includes a movement control unit 312, an acquisition unit 314, a detection unit 316, a reception unit 318, a calibration unit 320, an abnormality detection unit 322, a correction unit 324, and a distribution generation unit 326. Note that in the present embodiment, an example in which the control unit 310 of the remote operation apparatus 300 includes the movement control unit 312, the acquisition unit 314, the detection unit 316, the reception unit 318, the calibration unit 320, the abnormality detection unit 322, the correction unit 324, and the distribution generation unit 326 is described. However, at least one of the movement control unit 312, the acquisition unit 314, the detection unit 316, the reception unit 318, the calibration unit 320, the abnormality detection unit 322, the correction unit 324, or the distribution generation unit 326 may be included in a control unit of another apparatus that is connected to a remote operation apparatus 300 other than the remote operation apparatus 300 via a network. For example, the movement control unit 312, the acquisition unit 314, and the detection unit 316 may be included in a control unit of apparatuses that are different from each other.

The movement control unit 312 controls the movement of the UAV 10. The movement control unit 312 controls the movement of the UAV 10 such that the UAV 10 flies at a predetermined altitude along a predetermined flight route. The movement control unit 312 controls the movement of the UAV 10 such that the UAV 10 flies at a latitude, a longitude, and an altitude along a predetermined flight route. The movement control unit 312 may transmit, to the UAV 10, a control instruction indicating a latitude, a longitude, and an altitude along the predetermined flight route. The movement control unit 312 may transmit the control instruction to the UAV 10 to control the feedback such that the UAV 10 flies at a latitude, a longitude, and an altitude along a predetermined flight route, based on location information of the UAV 10 indicating the latitude, the longitude, and the altitude of the UAV 10 from the UAV 10.

The movement control unit 312 may calculate the speed of the UAV 10 when controlling the movement of the UAV 10. When the movement control unit 312 calculates the speed of the UAV 10, the speed may be a position displacement amount per unit time from location information of the GPS, the speed may be an integrated value of acceleration, the speed may be estimated from power input information to the propelling unit 40, the speed may be calculated from a measurement value of an anemometer, or the speed may be estimated by performing these operations together. As a composite operation, a Kalman filter may be used, for example.

If a no fly zone exists in a part of a target area, the movement control unit 312 may control the movement of the UAV 10 such that the UAV 10 flies avoiding the no fly zone.

The acquisition unit 314 acquires a measurement result of target gas that is obtained by a measurement by the gas sensor 70 while the UAV 10 is moving over the target area. The expression "while the UAV 10 is moving" means a state in which the UAV 10 is moving upward, moving downward, acceleration, deceleration, moving forward, moving backward, or pivoting, rather than a state in which the UAV 10 is hovering and maintaining a constant latitude, longitude, and altitude.

The acquisition unit 314 may further acquire, from the UAV 10, the location information of the UAV 10 when the measurement result is acquired from the gas sensor 70. The location information may be a position of the UAV 10 at any time point between a measurement start time and a measurement end time in one gas concentration measurement performed by the gas sensor 70. The location information may indicate the position of the UAV 10 at the measurement start time in one gas concentration measurement performed by the gas sensor 70. The location information may indicate the position of the UAV 10 at the measurement end time in one gas concentration measurement performed by the gas sensor 70. The location information may indicate a position of the UAV 10 at an intermediate time point between a measurement start time and a measurement end time in one gas concentration measurement performed by the gas sensor 70. When the gas sensor 70 has a response time T from the start of the measurement until an output of the measurement result by the gas sensor 70 due to gas replacement and the like, the acquisition unit 314 may acquire the response time T. Note that the response time T is a time from the start of the measurement until the output of the measurement result by the gas sensor 70, may be a replacement time calculated based on a diffusion coefficient of the target gas and a shape of a gas chamber of the gas sensor 70, may be a response delay time caused by a signal processing, may be a response delay time of the signal processing especially caused by time moving average/smoothing process, or may be a combined time of those.

The response time T may be input from outside, the response time T may be a value or expression set in advance, or may be individually estimated based on the measurement result of the gas sensor 70. For example, the response time T may be decided by acquiring gas concentration distributions in the same area in a plurality of conditions (speed, movement direction, wind direction), setting the response time T as a parameter, and optimizing the gas concentration distributions acquired in the plurality of conditions to match each other. The acquisition unit 314 may correct the measurement time with the response time T. In addition, the acquisition unit 314 may correct the location information at a certain time considering the response time. Specifically, the correction may be subtracting the response time T from the time t. In this manner, the distribution generation unit 326 described below can calculate the distribution of the target gas at the certain time more accurately.

Figure 4A:
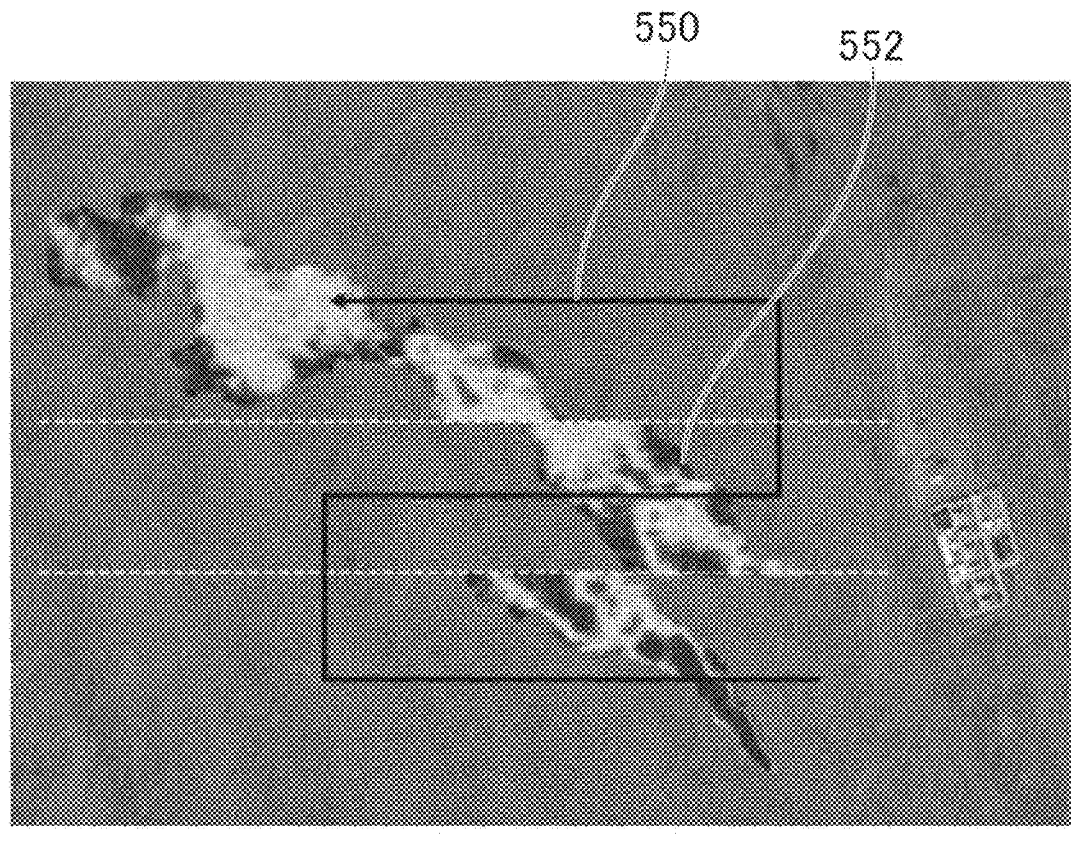
FIG. 4A shows an example of gas concentration distribution information to which correction according to response time is not applied.
Figure 4B:
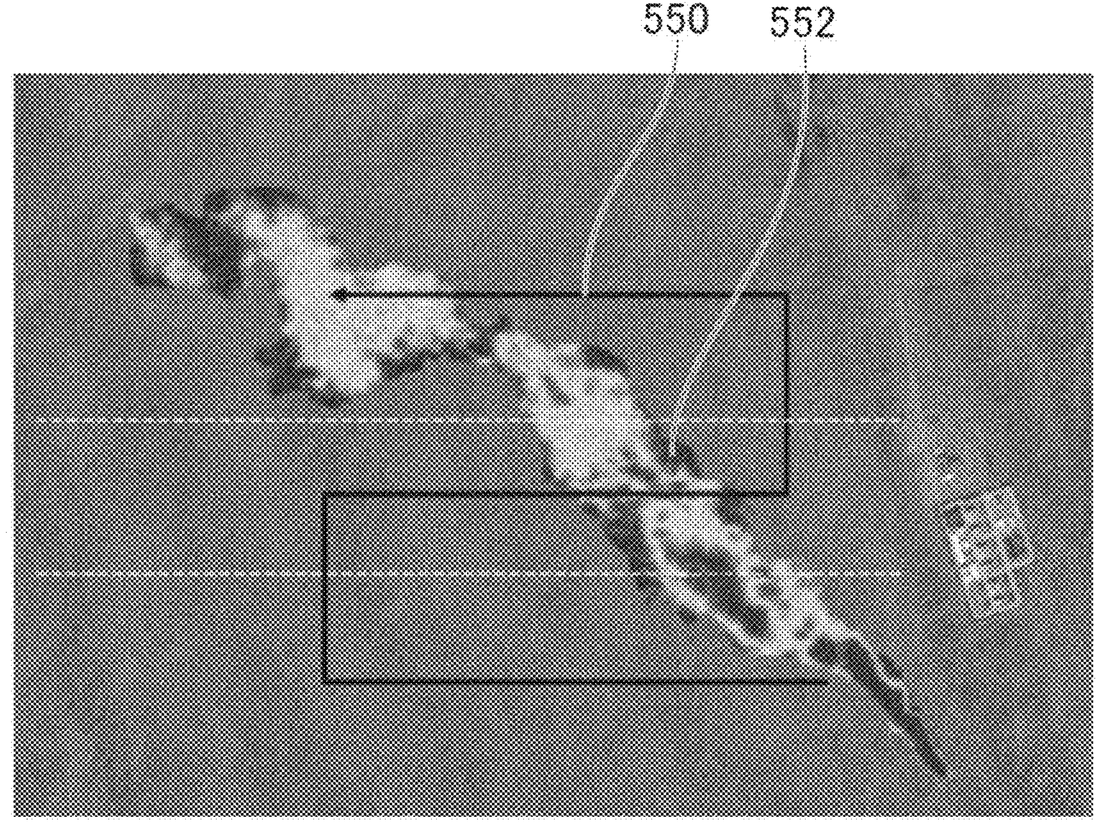
FIG. 4B shows an example of gas concentration distribution information to which correction according to response time is applied.

For example, in a relationship between the movement direction of the UAV 10 and the wind direction, due to the movement direction of the UAV 10, a deviation may occur in a correspondence between the location information and the measurement result. FIG. 4A shows an example of gas concentration distribution information generated by a distribution generation unit 326 without correcting the measurement time of the gas sensor 70 with the response time T. As shown in FIG. 4A, when the distribution generation unit 326 generates the gas concentration distribution information based on the measurement result that is obtained by the gas sensor 70 measuring the gas concentration while the UAV 10 is moving along a flight path 550, in a region 552 in which the movement direction of the UAV 10 is a reverse direction, the deviation in the correspondence between the location information and the measurement result may occur. In such a case, the acquisition unit 314 may correct the measurement time with the response time T. The acquisition unit 314 may eliminate the deviation in the correspondence between the location information and the measurement result caused by a difference in the movement direction of the UAV 10 by correcting the measurement time with the response time T. In this manner, as shown in FIG. 4B, the distribution generation unit 326 can generate the gas concentration distribution information by eliminating the deviation in the correspondence between the location information and the measurement result in the region 552 in which the movement direction of the UAV 10 is the reverse direction. Whether to perform the correction with the response time may be identified by the user. For example, the display unit displays the gas concentration distribution information before performing the correction according to the response time, and then whether to perform the correction according to the response time may be selected by the user. The acquisition unit 314 may correct the measurement time into the response time T when the user selects to perform the correction with the response time.

In addition, the acquisition unit 314 may correct the location information at a certain time considering the speed of the UAV 10. For example, if a position vector x indicating the location information of the UAV 10 is set, a velocity vector v of the UAV 10 is set, a response time T of the gas sensor 70 is set, and a correction position vector xc indicating the location information of the UAV 10 that is obtained by correction is set, $xc=x-vT$ may be satisfied. In addition, x, v, T may be information obtained by performing a statistical process on the measurement result. In addition, the velocity vector v may be a difference between a velocity vector of the UAV 10 and a vector of the wind direction. In addition, the correction position vector xc is location information of the UAV 10 that is obtained by correction and a position coordinate that is obtained by correcting each measurement result of the gas sensor 70 at the same time, but in correcting each xc, each x, and v, T at each time point t may be corrected by estimating using data in a spatial/temporal vicinity. More specifically, each x, and v, T at each time point t may be predicted and corrected by using data assimilation/inverse analysis.

The acquisition unit 314 may further acquire, from the UAV 10, the measurement result of the wind direction and the wind speed from the anemometer 80 to the UAV 10. The acquisition unit 314 may further acquire environment information indicating an environment state of the surroundings of the UAV 10. The acquisition unit 314 may further acquire, from the UAV 10, the environment information indicating the temperature of the surroundings of the UAV 10 measured at the temperature sensor 45 and the humidity of the surroundings of the UAV 10 measured at the humidity sensor 46.

The movement control unit 312 may control, based on the measurement result of the anemometer 80, the movement of the UAV 10 such that the UAV 10 moves from a downwind direction toward an upwind direction over the target area.

The detection unit 316 detects the leakage of the target gas in the target area based on the measurement result of the gas sensor 70. The accuracy of the measurement result that is obtained by a measurement by the gas sensor 70 may change depending on the environment, for example, temperature, humidity, and the like of the surroundings of the gas sensor 70. Accordingly, when the environment, for example, the temperature or the humidity of the surroundings of the gas sensor 70 satisfies a predetermined condition, the detection unit 316 may detect the leakage of the target gas in the target area based on the measurement result of the gas sensor 70. The detection unit 316 may identify a gas leakage spot at which the leakage of the target gas is detected in the target area based on the measurement result of the gas sensor 70 and the location information of the UAV 10. The detection unit 316 may identify the gas leakage spot at which the leakage of the target gas is detected in the target area based on the measurement result and the response time of the gas sensor 70 and the location information of the UAV 10. The detection unit 316 may correct the location information at a certain time based on the response time. The detection unit 316 may identify the gas leakage spot based on location information from the time at which the gas sensor 70 outputs the measurement result to the time before the response time of the gas sensor 70. That is, the detection unit 316 may identify the gas leakage spot based on the location information at the time that is obtained by subtracting the response time T of the gas sensor 70 from the time at which the gas sensor 70 outputs the measurement result.

When the UAV 10 performs a measurement of the gas concentration by the gas sensor 70 while moving, the measurement accuracy of the gas sensor 70 may decrease compared to a case in which the UAV 10 performs the measurement of the gas concentration by the gas sensor 70 while hovering.

Therefore, the detection unit 316 detects a gas leakage candidate area in which the gas leakage may occur first, based on the measurement result that is obtained by the measurement of the gas sensor 70 while the UAV 10 is moving at a first velocity. Next, based on a measurement result that is obtained by the measurement by the gas sensor 70 while the UAV 10 is moving over the gas leakage candidate area at a second velocity slower than the first velocity, or obtained by the measurement of the gas sensor 70 while the UAV 10 is stopped at the gas leakage candidate area, a gas leakage spot may be identified from the gas leakage candidate area. The size of the gas leakage spot may be determined based on the distance for which the UAV 10 moves during one measurement of the target gas by the gas sensor 70. The size of the gas leakage spot may be an area within a predetermined radius in which the position of the UAV 10 is the center. The predetermined radius may be determined based on the altitude at which the UAV 10 flies during the measurement of the gas sensor 70. The predetermined radius may be determined based on the height between an object of which gas leakage is to be detected and the UAV 10. The predetermined radius may be less as the height between an object of which gas leakage is to be detected and the UAV 10 is lower. That is, the nearer the UAV 10 to the object of which gas leakage is to be detected, the predetermined radius may be less.

The movement control unit 312 causes the gas sensor 70 to measure the gas concentration with a first spatial resolution while causing the UAV 10 to move at a first velocity. The detection unit 316 determines whether a gas leakage candidate area exists, in which a gas concentration of the target gas based on the measurement result that is obtained by the measurement by the gas sensor 70 while the UAV 10 is moving at the first velocity satisfies a first condition. The detection unit 316 may determine that the gas leakage candidate area in which the gas concentration satisfies the first condition exists when the gas concentration of the target gas is greater than or equal to a first threshold. When the gas leakage candidate area exists, the movement control unit 312 controls the movement of the UAV 10 such that the UAV 10 moves over the gas leakage candidate area at a second velocity that is slower than the first velocity or the UAV 10 stops at the gas leakage candidate area.

The movement control unit 312 may control the movement of the UAV 10 to measure the gas concentration obtained by the gas sensor 70 while making the UAV 10 move upward or move downward. The movement control unit 312 may control the movement of the UAV 10 to make the UAV 10 move upward or move downward while pivoting. In this manner, it is difficult for gas to be taken into the intake of the gas sensor 70 by down wash, and the gas concentration can be prevented from being not measured accurately.

The acquisition unit 314 acquires an additional measurement result of the target gas that is obtained by the measurement by the gas sensor 70 while the UAV 10 is moving at the second velocity over the gas leakage candidate area or stopped in the gas leakage candidate area. The detection unit 316 determines whether the gas concentration of the target gas based on the additional measurement result satisfies a second condition. The detection unit 316 may determine that the gas concentration satisfies the second condition when the gas concentration of the target gas based on the additional measurement result is greater than or equal to a second threshold. The second threshold may be the same as the first threshold. Alternatively, the second threshold may be higher than the first threshold. When the gas concentration of the target gas based on the additional measurement result satisfies the second condition, the detection unit 316 identifies that the gas leakage candidate area is a gas leakage spot.

Due to a weight difference between the target gas and the air, the gas concentration may change depending on the altitude. Therefore, based on the measurement result that is obtained by the measurement by the gas sensor 70 while the movement control unit 312 is making the UAV 10 move at the first velocity over the target area while maintaining the first altitude, the detection unit 316 first detects a gas leakage candidate area in which there may occur a gas leakage. Next, based on a measurement result that is obtained by the gas sensor 70 while the UAV 10 is moving over the gas leakage candidate area at a second velocity that is slower than the first velocity while maintaining a second altitude that is different from the first altitude, or obtained by the measurement by the gas sensor 70 while the UAV 10 is stopped in the gas leakage candidate area while maintaining the second altitude, the detection unit 316 may identify the gas leakage spot from the gas leakage candidate area.

Because the target gas tends to be distributed in a wider area at higher altitude due to natural diffusion, the second altitude may be lower than the first altitude, and the second threshold may be higher than the first threshold.

When the target gas is heavier than the air, the second altitude may be lower than the first altitude, and the second threshold may be higher than the first threshold. When the target gas is lighter than the air, the second altitude may be higher than the first altitude, and the second threshold may be higher than the first threshold.

When a gas leakage candidate area exists, in which gas concentration of the target gas based on the measurement result that is obtained by the measurement by the gas sensor 70 while the UAV 10 is moving over the target area at a first velocity while maintaining the first altitude satisfies the first condition, the movement control unit 312 may control the movement of the UAV 10 such that the UAV 10 moves over the gas leakage candidate area at a second velocity that is slower than the first velocity while maintaining a second altitude that is different from the first altitude, or the UAV 10 stops in the gas leakage candidate area while maintaining the second altitude. The acquisition unit 314 may acquire an additional measurement result of the target gas that is obtained by the measurement by the gas sensor 70 while the UAV 10 is moving at the second velocity while maintaining the second altitude over the gas leakage candidate area or stopped in the gas leakage candidate area while maintaining the second altitude. When the gas concentration of the target gas based on the additional measurement result satisfies the second condition, the detection unit 316 may identify that the gas leakage candidate area is a gas leakage spot.

When the detection unit 316 identifies the gas leakage spot, the acquisition unit 314 may capture the gas leakage spot in the image capturing apparatus 30 and acquire the captured image as an image of the gas leakage spot from the UAV 10. When the target gas has a light absorption characteristic at an infrared region, the image capturing apparatus 30 may be an infrared imaging apparatus (infrared camera). When the target gas emits light of a specific wavelength band, the image capturing apparatus 30 may be an imaging apparatus having a sensitivity for that wavelength band. Specifically, when the target gas is hydrogen, because ultraviolet is emitted at the time of combustion, the image capturing apparatus 30 may be an ultraviolet camera.

Figure 5:
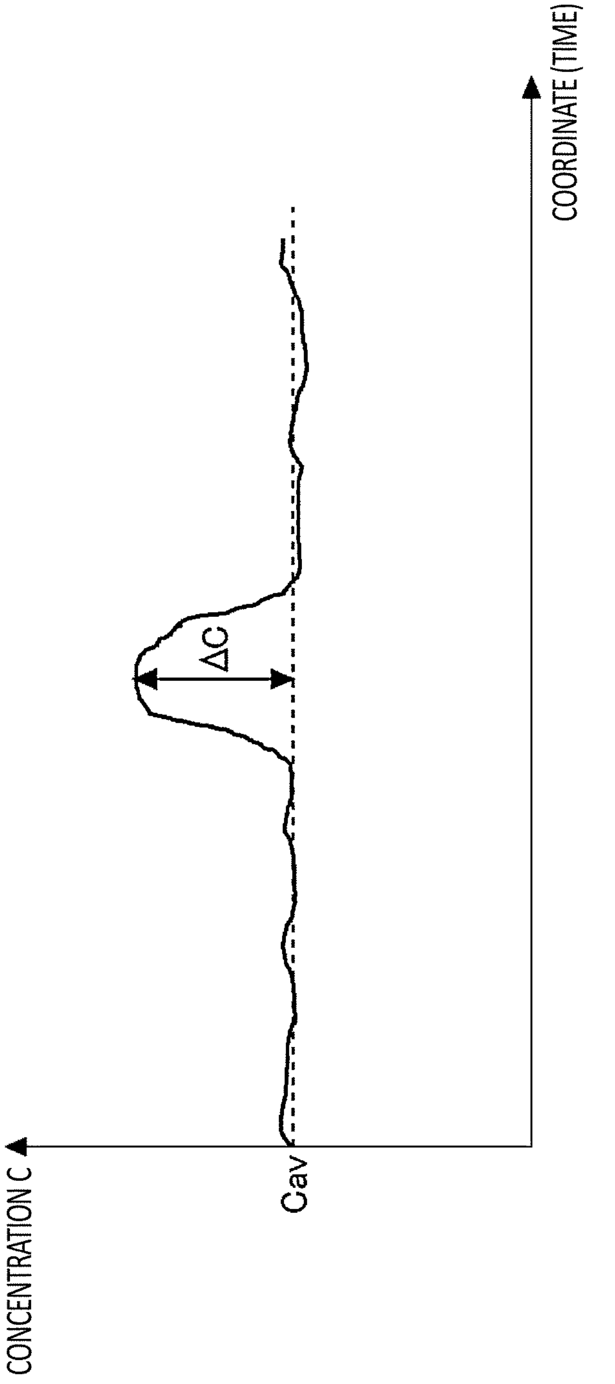
FIG. 5 shows an example of the state of change depending on the coordinate (time) of gas concentration.

The movement control unit 312 may control the movement of the UAV 10 such that the UAV 10 moves over the target area for multiple times. The movement control unit 312 may control the flight of the UAV 10 such that the UAV 10 flies over the target area along a predetermined flight route for multiple times. The detection unit 316 may detect a leakage of the target gas for each area based on a gas concentration of the target gas based on the measurement result of each area in the target area. The detection unit 316 may detect a leakage of the target gas for each area based on an average value of the gas concentration of the target gas of each area based on the measurement result of each area in the target area. For example, as shown in FIG. 5, the detection unit 316 may detect an area in which a difference AC from an average value Cav of the gas concentration of the target gas of each area based on the measurement result of each area in the target area is greater than or equal to a threshold as a gas leakage spot. The detection unit 316 may detect, when the target area is moved for multiple times, the area as a gas leakage spot after confirming that AC is reproduced in a reference.

The detection unit 316 may detect the leakage of the target gas based on a rate of change of the gas concentration of the target gas based on the measurement result that is obtained by the measurement by the gas sensor 70 while the UAV 10 is moving. The detection unit 316 may detect the leakage of the target gas when a rate of change of the gas concentration of the target gas based on the measurement result that is obtained by the measurement by the gas sensor 70 while the UAV 10 is moving is greater than or equal to a threshold.

The detection unit 316 may detect the leakage of the target gas based on a differential value of the gas concentration of the target gas based on the measurement result that is obtained by the measurement by the gas sensor 70 while the UAV 10 is moving.

By performing a statistical process on data of the gas concentration of the target gas based on the measurement result that is obtained by the measurement by the gas sensor 70 while the UAV 10 is moving, the detection unit 316 may calculate a level of deviation, as a degree of deviation from a statistical average, with respect to data of the gas concentration of the target gas obtained from moment to moment, and detect the leakage of the gas based on the level of deviation. Specifically, the level of deviation may be defined as a level of deviation $\alpha=(x-\mu)^2/\sigma^2$ with respect to new gas concentration data x by calculating, with respect to the data of the gas concentration of the target gas or data of a rate of change of the gas concentration data, an average value $\mu$ or a distribution $\sigma^2$ of the time or position in an appropriate section, may be detected as a leakage of the target gas by determining a new gas concentration data x as statistically abnormal when the level of deviation defined in such a manner exceeds an appropriate threshold, and the threshold may be 9, 16 or 36.

The detection unit 316 may detect the leakage of the target gas for each area based on a comparison between each gas concentration of the target gas based on the measurement result of each area in the target area and an average value of the gas concentration of the target gas based on the measurement result of the entire area of the target area. The detection unit 316 may detect an area in which the gas concentration is higher by a threshold or more than that of the average value of the gas concentration of the target gas based on the measurement result of the entire area of the target area as a gas leakage spot of the target gas.

The detection unit 316 may detect the leakage of the target gas by using not only the measurement result of the gas sensor 70 provided from a plurality of UAVs 10 but at least one of measurement information of a stationary gas sensor or observation information of an artificial earth satellite. A measurement principle of the stationary gas sensor may be a non-dispersive infrared absorption method, Tunable Diode Laser Absorption Spectroscopy (TDLAS), DIAL (Differential Absorption LiDAR), TCSPC (Time Correlated Single Photon Counting), a photoacoustic method, a semiconductor method, a solid electrolyte method, a thermal conduction method, an acoustic wave method, an optical gas imaging method, or a capacitance method. The observation information of the artificial earth satellite may be observation information such as visible ray, infrared or microwave that is reflected/emitted from the ground, ocean, atmosphere and the like, or may be observation information of a reflected wave that is obtained by irradiating an electromagnetic wave toward an object to-be-observed.

The reception unit 318 receives a spatial resolution of the gas leakage detection. The spatial resolution may be the distance between two points of which measurement results of the gas sensor 70 are independent or may be the size of one pixel in a case a gas distribution is indicated. The reception unit 318 receives the spatial resolution of the gas leakage detection from a user. The movement control unit 312 controls the movement of the UAV 10 such that the UAV 10 moves at a speed based on the spatial resolution. The movement control unit 312 may divide a spatial resolution (m) by a response time (T) that indicates the time it takes for the gas sensor 70 detecting one gas concentration, to derive m/T, and decide the speed of the UAV 10 based on m/T. The movement control unit 312 may perform multiplication of the speed (v) of the UAV 10 and the response time (T), to decide the distance of the spatial resolution. The speed (v) may be obtained by statistically processing the speed during the flight. For example, the statistical process may be a time sequence average. The response time (T) is a time from the start of the measurement until the output of the measurement result by c, may be a replacement time calculated based on a diffusion coefficient of the target gas and a shape of a gas chamber of the gas sensor 70, may be a response delay time caused by a signal processing, or may be a combined time of those.

A characteristic of the gas sensor 70 may change over a lapse of time. Therefore, the gas sensor 70 is preferably periodically calibrated. Therefore, the movement control unit 312 may periodically move an area outside the target area, which is not subjected to the effect of the gas even though a gas leakage occurs in the target area, to the UAV 10, to perform a calibration. When an error occurs in the measurement result of the gas sensor 70, the movement control unit 312 may move an area outside the target area, which is not subjected to the effect of the gas even though a gas leakage occurs in the target area, to the UAV 10.

The acquisition unit 314 may further acquire a measurement result of target gas that is obtained by the measurement by the gas sensor 70 while the UAV 10 is moving over the area outside the target area. The calibration unit 320 performs the calibration of the gas sensor based on the measurement result of the area outside the target area. The measurement result of the area outside the target area has a high possibility of matching with the gas concentration of the target gas of a case in which the gas leakage does not occur. Therefore, the calibration unit 320 decides a correction factor for correcting the measurement result of the gas sensor 70 or a correction amount such that the gas concentration based on the measurement result of the area outside the target area matches a predetermined gas concentration of the target gas of a case in which the gas leakage does not occur. The detection unit 316 corrects and derives the gas concentration based on the measurement result that is obtained by the gas sensor 70, based on the correction factor or the correction amount decided by the calibration unit 320.

When the correction factor or the correction amount decided by the calibration unit 320 is large, the gas sensor 70 may be abnormal. Therefore, when the correction factor or the correction amount decided by the calibration unit 320 is larger than a predetermined reference, the calibration unit 320 may output a warning signal indicating that the gas sensor 70 is abnormal without performing the calibration. Herein, the calibration unit 320 may dynamically set the predetermined reference based on the correction amount of the calibration performed in the past.

In the area in which the gas leakage occurs, the detection of the gas leakage may be preferably performed continuously or periodically. Therefore, the movement control unit 312 may control the UAV 10 such that the UAV 10 repeats the movement of the gas leakage spot. Each time the UAV 10 moves the gas leakage spot, the acquisition unit 314 may acquire a measurement result of the target gas that is obtained by the measurement by the gas sensor 70. Each time the acquisition unit 314 acquires the measurement result of the gas leakage spot, the detection unit 316 may detect the leakage of the target gas at the gas leakage spot.

When an area in which a risk of gas leakage is high is a focused area, in the focused area, the detection of the gas leakage may be preferably performed intensively or periodically. Therefore, the movement control unit 312 may control the UAV 10 such that the UAV 10 moves intensively over the focused area or move repeatedly. Specifically, the focused area may be a peripheral area that is at least one of a pipeline joint, a pit mouth of a gas well, a flare system, a vent mouth, a pumping apparatus, and a chimney. In an area other than the focused area, the UAV 10 may fly at a first velocity, and fly at a second velocity that is slower than the first velocity in the focused area.

When the UAV 10 measures the gas concentration by the gas sensor 70 while moving, because the measurement is not performed continuously at one point, the gas concentration measured by the gas sensor 70 has a high possibility of varying. If the gas concentration obtained by measurement of the gas sensor 70 does not change even though the measurement is performed by a gas concentration by the gas sensor 70 while the UAV 10 is moving, the gas sensor 70 may be abnormal. Therefore, the abnormality detection unit 322 senses the abnormality of the gas sensor 70 when the concentration of the target gas based on the measurement result that is obtained by the measurement by the gas sensor 70 while the UAV 10 is moving does not change over a predetermined period, or an amount of change is in a predetermined range. In this manner, the abnormality of the gas sensor 70 can be found early.

When the UAV 10 flies outside the target area in which the gas leakage does not occur, if a identified value of the measurement result of the gas sensor 70 is also high, or if the measurement result is not output, because the gas sensor 70 has a high possibility of abnormality, the abnormality detection unit 322 may sense the abnormality of the gas sensor 70.

The correction unit 324 corrects an error that is generated on the measurement result of the target gas that is obtained by the measurement by the gas sensor 70 due to a noise generated by driving of a drive source of the UAV 10 with a correction amount depending on the speed of the UAV 10. The drive source is a motor for rotating a rotary wing, for example. A noise such as an electromagnetic noise generated by the driving of the motor may affect a signal indicating the measurement result output from the gas sensor 70 to generate an error on the measurement result. Such a noise tends to be increased as an amount of rotation of the motor is large. That is, depending on the speed of the UAV 10, the size of the noise tends to be changed. Therefore, the correction unit 324 may decide a correction amount depending on the speed of the UAV 10 with reference to relationship information indicating a relationship between the speed of the UAV 10 and the correction amount, and correct the gas concentration based on the measurement result that is obtained by the gas sensor 70 with the decided correction amount. Under an instruction of correction, the correction unit 324 may decide a correction amount depending on the speed of the UAV 10 with reference to relationship information indicating a relationship between the speed of the UAV 10 and the correction amount, and correct the gas concentration based on the measurement result that is obtained by the gas sensor 70 with the decided correction amount. Without the instruction of correction, the correction unit 324 may derive the gas concentration based on the measurement result that is obtained by the gas sensor 70 without correcting the measurement result that is obtained by the gas sensor 70. For example, a gas concentration before the correction is displayed on a display unit included in the remote operation apparatus 300, the remote operation apparatus 300 receives an instruction of correction when a user determines that the gas concentration is an abnormal value, the correction unit 324 may decide, under the instruction of correction, a correction amount depending on the speed of the UAV 10 with reference to relationship information indicating a relationship between the speed of the UAV 10 and the correction amount, and correct the gas concentration based on the measurement result that is obtained by the gas sensor 70 with the decided correction amount.

In addition, the gas sensor 70 may perform a sampling of gas at a frequency that is faster than a drive frequency of the drive source. By the gas sensor 70 performing the sampling of gas at the frequency that is faster than the drive frequency of the drive source, the effect of the electromagnetic noise generated from the drive source can be reduced. For example, when the gas sensor 70 is an NDIR gas sensor, the effect of the electromagnetic noise generated from the drive source can be reduced by making a drive frequency of a light source quicker than the drive frequency of the drive source.

Figure 6:
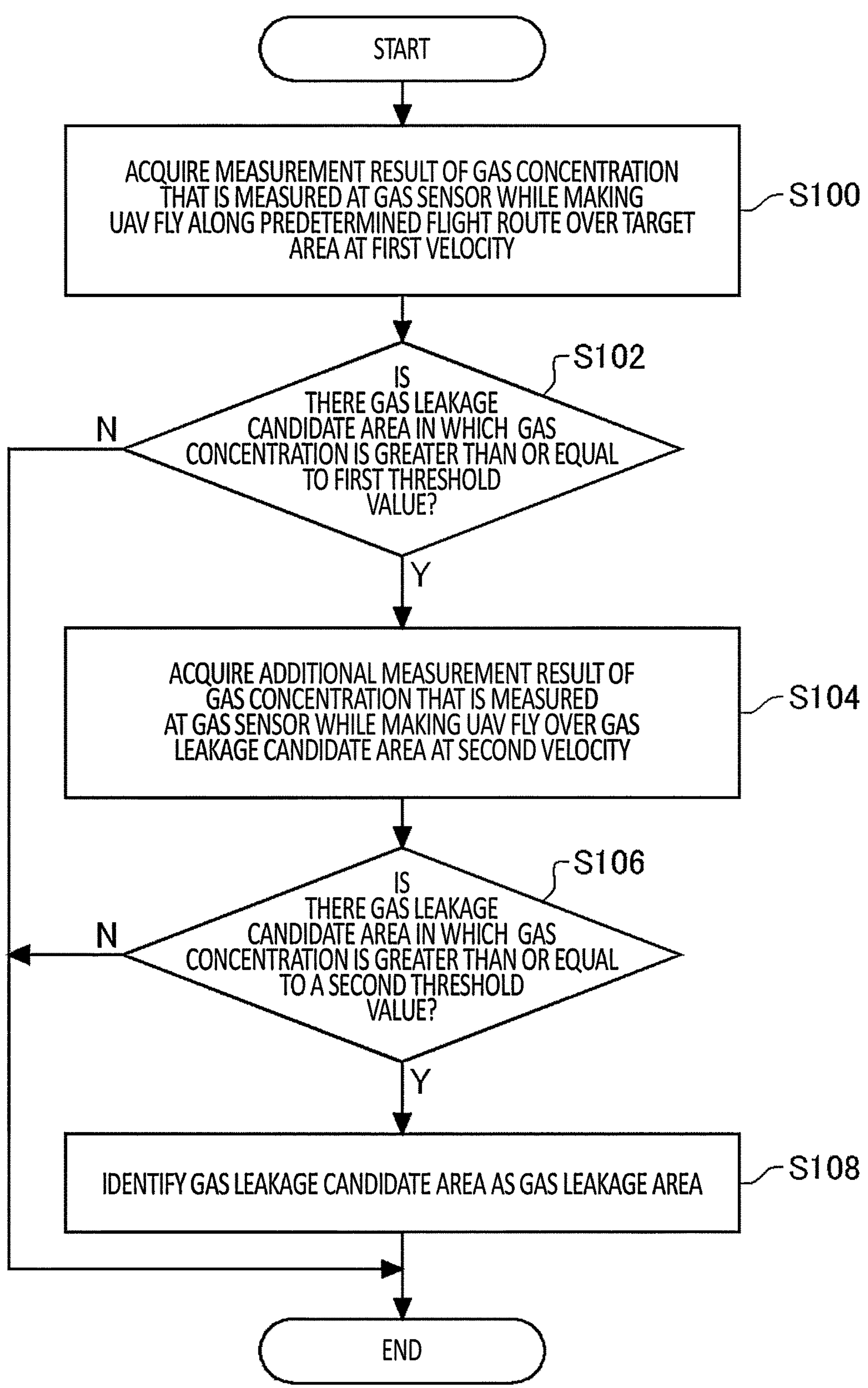
FIG. 6 is a flowchart showing an example of a gas leakage detection procedure.

FIG. 6 is a flowchart showing an example of a gas leakage detection procedure. While the movement control unit 312 is making the UAV 10 fly along a predetermined flight route over a target area at a first velocity, the acquisition unit 314 acquires a measurement result of a gas concentration that is measured at the gas sensor 70 (S100).

Detection unit 316 determines whether there is a gas leakage candidate area in which the gas concentration based on the measurement result is greater than or equal to a first threshold (S102). The detection unit 316 may identify a gas leakage spot in which the gas concentration based on the measurement result is greater than or equal to the first threshold, based on location information of the UAV 10 that is acquired by the acquisition unit 314 along with the measurement result.

When the gas leakage candidate area exists, the acquisition unit 314 acquires an additional measurement result of the gas concentration that is measured at the gas sensor 70 while the movement control unit 312 is making the UAV 10 fly over the gas leakage candidate area at a second velocity that is slower than the first velocity (S104).

Detection unit 316 determines whether there is a gas leakage candidate area in which the gas concentration based on the additional measurement result is greater than or equal to a second threshold (S106). When a gas leakage candidate area with the gas concentration greater than or equal to the second threshold exists, the detection unit 316 identifies a gas leakage candidate area in which the gas concentration is greater than or equal to the second threshold as a gas leakage spot (S108).

By such a procedure, the detection unit 316 detects the presence or absence of the gas leakage of the entire target area with a relatively low spatial resolution, and then further specifically detects the presence or absence of the gas leakage of a gas leakage candidate area, in which there is a high possibility of gas leakage, at a relatively high spatial resolution. In this manner, prevention of decreasing in the accuracy of the gas leakage detection can be performed early, while detecting the presence or absence of the gas leakage in the entire target area.

The distribution generation unit 326 may generate gas distribution information of the gas concentration of the target area based on each measurement result in the target area. The distribution generation unit 326 may identify, based on the gas distribution information, a safe area in which a human body is not affected and indicate the safe area on the gas distribution information.

When a gas leakage of a relatively wide target area such as a pipeline is detected, if a gas leakage in the entire target area is detected by using one UAV 10 it may take a long time until the detection of the gas leakage of all of the entire target area is completed.

Therefore, the remote operation apparatus 300 may control the flight of a plurality of UAVs 10 and the detection of the gas leakage of the target area may be shared by the plurality of UAVs 10.

The plurality of UAVs 10 may perform a measurement of the target gas at each gas sensor 70 while flying over at least one target area assigned from a plurality of target areas included in the entire target area. That is, the movement control unit 312 may measure the gas concentration of the target gas at each gas sensor 70 while making each of the plurality of UAVs 10 fly over at least one target area assigned from the plurality of target areas included in the entire target area.

Figure 7:
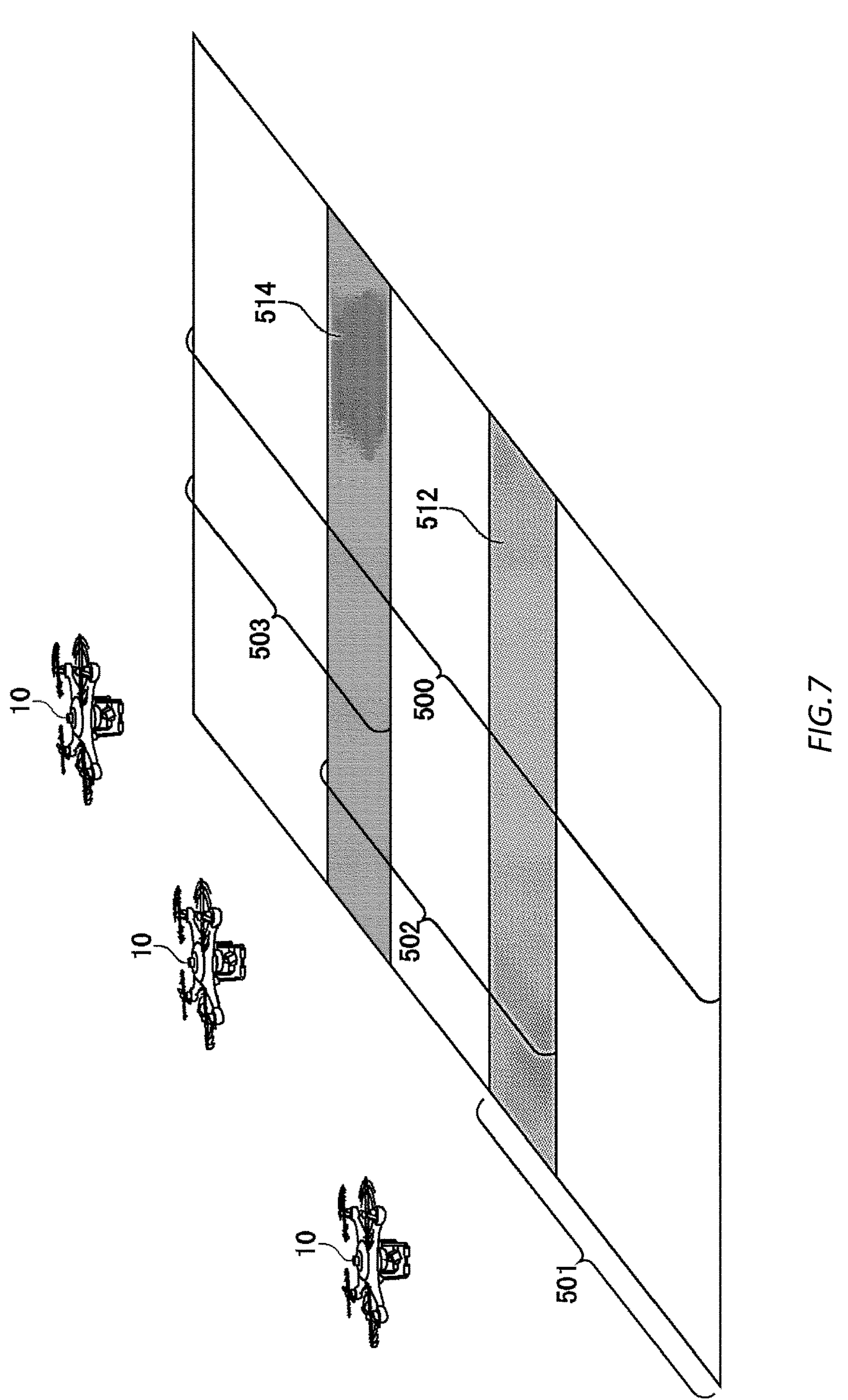
FIG. 7 is a diagram for describing a gas leakage detection method using a plurality of UAVs.

For example, as shown in FIG. 7, the UAV 10 is assigned for each target area 501, 502, 503 after dividing an entire target area 500 into three target areas 501, 502, 503. Furthermore, the movement control unit 312 performs measurement of a gas concentration of the target area 501, 502, 503 at each gas sensor 70 while making each UAV 10 fly over each of the target area 501, 502, 503.

The distribution generation unit 326 generates gas distribution information of the target gas in the entire target area based on a measurement result of each gas sensor 70 in each target area 501, 502, 503 provided from the plurality of UAVs 10.

As shown in FIG. 7, each of the plurality of target areas 501, 502, 503 may have overlapping areas 512, 514 each overlap with an adjacent target area. In this case, the distribution generation unit 326 may generate the gas distribution information by deriving a gas concentration of the target gas of each of the overlapping areas 512, 514 based on the measurement result of each gas sensor 70 provided from each UAV 10 that moves over each of the overlapping areas 512, 514. The distribution generation unit 326 may generate the gas distribution information of the overlapping areas 512, 514 based on an average value of gas concentration or distribution information that are based on the measurement result of each gas sensor 70 provided from each UAV 10 moving over the overlapping areas 512, 514.

The distribution generation unit 326 may generate the gas distribution information by deriving the gas concentration with which residual error from each measurement result group of the overlapping area 512 provided from each UAV 10 moving over the overlapping area 512 is minimized. The distribution generation unit 326 may generate the gas distribution information by deriving the gas concentration with which a sum of squares of the residual error (sum of squares difference) from each measurement result group of the overlapping area 512 provided from each UAV 10 moving over the overlapping area 512 is minimized. For example, when a measurement result group of the gas sensor 70 in the overlapping area 512 included in the target area 501 is V501 and a measurement result group of the gas sensor 70 in the overlapping area 512 included in the target area 502 is V502, the distribution generation unit 326 may generate gas distribution information by deciding, with respect to V501 and V502, a predicted gas concentration distribution VP such that a level of deviation is minimized. Specifically, the distribution generation unit 326 may generate the gas distribution information by calculating a residual error between a predicted concentration distribution VP and each of V501 and V502, taking a residual sum of squares, and calculating a predicted concentration distribution such that the residual sum of squares is minimized, more specifically, when the predicted concentration VP is characterized by a parameter, the distribution generation unit 326 may generate gas distribution information by deciding the parameter such that the residual sum of squares is minimized.

By comparing the measurement result of each gas sensor 70 provided from each UAV 10 moving over each of the overlapping areas 512, 514, the distribution generation unit 326 may derive a correction factor for correcting the measurement result of each gas sensor 70 or a correction amount such that each measurement result matches each other. The distribution generation unit 326 may derive the gas concentration of the target area by correcting the measurement result of each target area with the correction factor or the correction amount. In this manner, an error in measurement results between the gas sensors 70 can be reduced, and a deviation in a gas concentration distribution at a boundary between the target areas can be reduced.

For example, when an average value AV 501 of a measurement result of the gas sensor 70 in the overlapping area 512 included in the target area 501 is set and an average value AV 502 of a measurement result of the gas sensor 70 in the overlapping area 512 included in the target area 502 is set, by subtracting (AV502−AV501) from the measurement result of the target area 502, the deviation in the gas concentration distribution at the boundary between the target areas can be reduced.

The distribution generation unit 326 may generate the gas distribution information by deriving the gas concentration with which residual error from each measurement result group provided from each UAV 10 moving over each target area is minimized. The distribution generation unit 326 may generate the gas distribution information by deriving the gas concentration with which a sum of squares of the residual error (sum of squares difference) from each measurement result group provided from each UAV 10 moving over each target area is minimized. For example, when the measurement result group of the gas sensor 70 of the target area 501 is V501 and the measurement result group of the gas sensor 70 of the target area 502 is V502, the distribution generation unit 326 may estimate baseline correction distribution information that is obtained when the gas does not exist, and generate gas distribution information based on a data difference between the measurement result group and the baseline gas correction distribution information, such that a level of deviation is minimized with respect to V501 and V502. Specifically, the distribution generation unit 326 may generate gas distribution information as the baseline correction distribution information, by assuming that a polynominal function or a Fourier series related to the position is a baseline correction distribution, calculating a residual error from each of V501 and V502, taking a sum of squares of the residual error, deciding a baseline gas distribution such that a residual sum of squares is minimized, and taking a difference between the obtained gas concentration and the baseline correction distribution.

Furthermore, the distribution generation unit 326 may interpolate and predict the gas concentration distribution by using an operation performed by the obtained gas concentration distribution and CFD (computation fluid dynamics), and further calculate the total amount of gas. Specifically, the distribution generation unit 326 may interpolate and predict a gas concentration distribution by performing data assimilation on a predicted value of the gas concentration distribution that is obtained by a four-dimensional variational method and the gas concentration distribution that is obtained by a CFD operation, and further calculate a total amount of gas. The total amount of gas that is calculated may be used as an amount of leaked gas. In addition, when the gas concentration distribution is interpolated and predicted, and the total amount of gas is further calculated: an inverse analysis may be performed by an adjoint analysis for the obtained gas concentration distribution; assuming that a gas leakage source exists in a localized manner rather than a distributed manner, the inverse analysis may be performed with a predictive indicator that the more localized the predicted position probability distribution of the gas leakage source is, the better the predict accuracy is; an entropy or an average information amount for a predicted position probability distribution of the leakage source may be added, as the predictive indicator, along with the obtained gas concentration distribution and an error of a predicted gas concentration distribution of the gas; and when a predicted position probability distribution function of the gas leakage source is $p(x)$ for a position x, an entropy H may be $H=-\int p(x) \log(p(x))$ (wherein the integration is for a total space).

The distribution generation unit 326 may calculate a gas concentration distribution or a total amount of gas by using not only the measurement result of the gas sensor 70 provided from a plurality of UAVs 10 but at least one of measurement information of a stationary gas sensor or observation information of an artificial earth satellite. A measurement principle of the stationary gas sensor may be a non-dispersive infrared absorption method, Tunable Diode Laser Absorption Spectroscopy (TDLAS), DIAL (Differential Absorption LiDAR), TCSPC (Time Correlated Single Photon Counting), a photoacoustic method, a semiconductor method, a solid electrolyte method, a thermal conduction method, an acoustic wave method, an optical gas imaging method, or a capacitance method. The observation information of the artificial earth satellite may be observation information such as visible ray, infrared or microwave that is reflected/emitted from the ground, ocean, atmosphere and the like, or may be observation information of a reflected wave that is obtained by irradiating an electromagnetic wave toward an object to-be-observed.

The gas leakage detection system may further include a reporting unit, which makes an electronic report of a gas leakage spot related to a facility of production/transportation/storage/consumption of the target gas or an amount of leaked gas, and reports the electronic report to an authentication system. The authentication system may authenticate the facility of production/transportation/storage/consumption of the target gas or an operator that controls the facility of production/transportation/storage/consumption of the target gas based on the reported electronic report. For example, if an amount of leaked gas in a period is less than or equal to a identified value, the authentication system may authenticate an operator that controls the facility of production/transportation/storage/consumption of the target gas as a good operator. In addition, the authentication system may use driving information of the facility of production/transportation/storage/consumption of the target gas in the authentication. The driving information may be a gas type, a gas production amount, a gas consumption amount, a gas transportation amount, a gas storage amount, a temporal change in the gas storage amount, a driving time, an energy consumption amount, a private power generation amount, a purchase power amount, an inspection record, repairing record, and an exhaust amount of greenhouse gas. In addition, at least one of the reported electronic report and the authentication result may be stored in a repository that can be also referred from a third party. For example, when the third party is an operator who consumes gas, a good operator who sells the gas may be selected based on the authentication result stored in the repository. In addition, the authentication system may issue a credit based on a difference between an amount of gas leaked during a period and a reference value. The credit is a carbon credit, for example.

Figure 8:
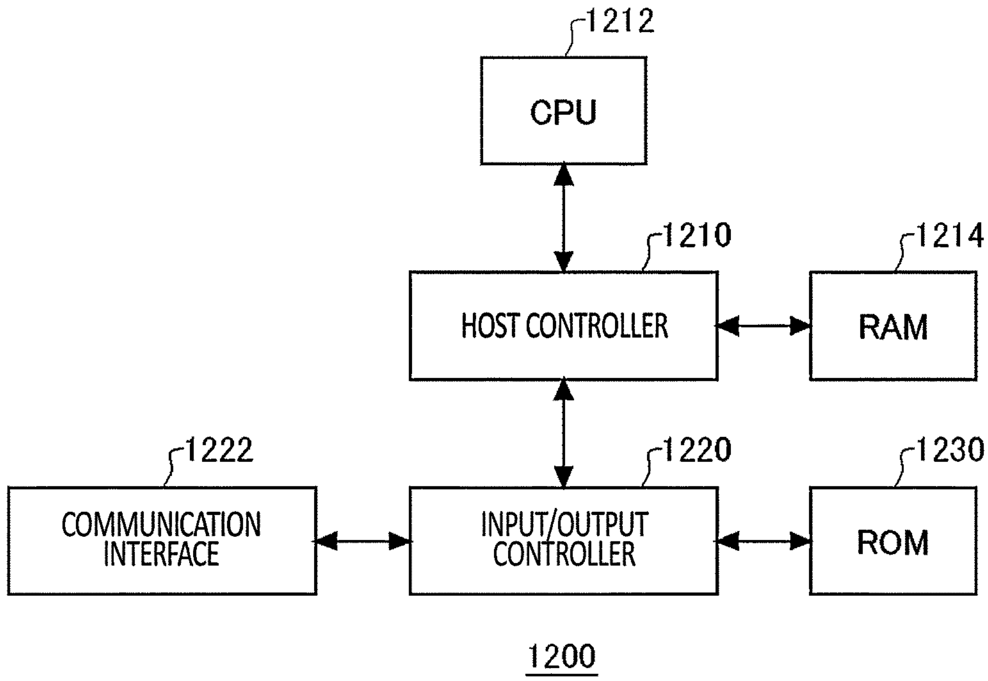
FIG. 8 shows an example of a hardware configuration.

FIG. 8 shows an example of a computer 1200 in which a plurality of aspects of the present invention may be embodied in whole or in part. Programs installed in the computer 1200 can cause the computer 1200 to function as operations associated with the apparatus according to the embodiments of the present invention or one or more "units" of the apparatus. Alternatively, the programs can cause the computer 1200 to execute the operations or the one or more "units". The programs can cause the computer 1200 to execute a process according to the embodiments of the present invention or steps of the process. Such programs may be executed by a CPU 1212 to cause the computer 1200 to perform specific operations associated with some or all of the blocks in the flowcharts and block diagrams described in the present specification.

The computer 1200 according to the present embodiment includes the CPU 1212 and a RAM 1214, which are mutually connected by a host controller 1210. The computer 1200 also includes a communication interface 1222 and an input/output unit, which are connected to the host controller 1210 via an input/output controller 1220. The computer 1200 also includes an ROM 1230.

The CPU 1212 operates according to the programs stored in the ROM 1230 and the RAM 1214, thereby controlling each unit.

The communication interface 1222 communicates with another electronic devices via a network. A hard disk drive may store the programs and data used by the CPU 1212 in the computer 1200. The ROM 1230 stores therein boot programs or the like executed by the computer 1200 at the time of activation, and/or programs depending on hardware of the computer 1200. A program is provided via a computer-readable recording medium such as a CD-ROM, a USB memory, or an IC card, or via a network. The programs are installed in the RAM 1214 or the ROM 1230 which is also an example of the computer-readable recording medium, and executed by the CPU 1212. Information processing described in these programs is read by the computer 1200, and provides cooperation between the programs and the various types of hardware resources described above. The apparatus or method may be configured by implementing operations or processings of information according to use of the computer 1200.

For example, if a communication is executed between the computer 1200 and an external device, the CPU 1212 may execute a communication program loaded in the RAM 1214 and instruct the communication interface 1222 to perform communication processing based on a process described in the communication program. The communication interface 1222, under the control of the CPU 1212, reads transmission data stored in a transmission buffer region provided in a recording medium such as the RAM 1214 or the USB memory, transmits the read transmission data to the network, or writes reception data received from the network to a reception buffer region or the like provided on the recording medium.

In addition, the CPU 1212 may cause all or necessary portions of a file or database stored in an external recording medium such as a USB memory, to be read by the RAM 1214, and execute various types of processings on the data on the RAM 1214. Next, the CPU 1212 may write the processed data back in the external recording medium.

Various types of information, such as various types of programs, data, tables, and databases, may be stored in the recording medium to undergo information processing. The CPU 1212 may execute, on the data read from the RAM 1214, various types of processing including various types of operations, information processing, conditional judgement, conditional branching, unconditional branching, information search/replacement, or the like described throughout the present disclosure and designated by instruction sequences of the programs, to write the results back to the RAM 1214. In addition, the CPU 1212 may search for information in a file, a database, or the like in the recording medium. For example, when a plurality of entries, each having an attribute value of a first attribute associated with an attribute value of a second attribute, are stored in the recording medium, the CPU 1212 may retrieve, out of the plurality of entries, an entry with the attribute value of the first attribute specified that meets a condition, read the attribute value of the second attribute stored in said entry, and thereby acquiring the attribute value of the second attribute associated with the first attribute satisfying a predetermined condition.

The programs or software modules described above may be stored in a computer readable storage medium on or near the computer 1200. In addition, a recording medium such as a hard disk or a RAM provided in a server system connected to a dedicated communication network or the Internet can be used as a computer readable storage medium, thereby providing a program to the computer 1200 via the network.

Computer readable medium may include any tangible device that can store instructions for execution by a suitable device. As a result, the computer readable medium having instructions stored therein includes an article of manufacture including instructions which can be executed to create means for performing operations specified in the flowcharts or block diagrams. Examples of the computer readable medium may include an electronic storage medium, a magnetic storage medium, an optical storage medium, an electromagnetic storage medium, a semiconductor storage medium, and the like. More specific examples of the computer readable medium may include a floppy (registered trademark) disk, a diskette, a hard disk, a random access memory (RAM), a read only memory (ROM), an erasable programmable read only memory (EPROM or a flash memory), an electrically erasable programmable read only memory (EEPROM (registered trademark)), a static random access memory (SRAM), a compact disc read only memory (CD-ROM), a digital versatile disk (DVD), a Blu-ray (registered trademark) disk, a memory stick, an integrated circuit card, and the like.

Computer-readable instructions may include either a source code or an object code written in any combination of one or more programming languages. The source code or the object code includes a conventional procedural programming language. The conventional procedural programming language may be assembler instructions, instruction-set-architecture (ISA) instructions, machine instructions, machine dependent instructions, microcode, firmware instructions, state-setting data, or an object-oriented programming language such as Smalltalk (registered trademark), JAVA (registered trademark), C++, etc., and programming languages, such as the "C" programming language or similar programming languages. The computer-readable instructions may be provided to a processor or a programmable circuit of a programmable data processing apparatus locally or via a local area network (LAN) or a wide area network (WAN) such as the Internet or the like. The processor or the programmable circuit may execute the computer-readable instructions to create means for performing operations specified in the flowcharts or block diagrams.

Here, the computer may be a computer such as a personal computer (PC), a tablet computer, smartphone, a workstation, a server computer, or a general purpose computer, or may be a computer system in which a plurality of computers are connected. Such computer system to which the plurality of computers are connected is also referred to as a distributed computing system, and is a computer in a broad sense. In a distributed computing system, a plurality of computers collectively execute a program by each of the plurality of computers executing a portion of the program, and passing data during the execution of the program among the computers as needed.

Examples of the processor include a computer processor, a central processing unit (CPU), a processing unit, a microprocessor, a digital signal processor, a controller, a microcontroller, and the like. The computer may include one processor or a plurality of processors. In a multi-processor system including a plurality of processors, the plurality of processors collectively execute a program by each of the processors executing a portion of the program, and passing data during the execution of the program among the processors as needed. For example, in execution of multiple tasks, each of the plurality of processors may execute a portion of each task pieces by pieces by performing task-switching for each time slice. In this case, which portion of one program each processor is responsible for executing dynamically changes. In addition, which portion of the program each of the plurality of processors is to execute may be statically determined by multi-processor aware programming.

While the present invention has been described with the embodiments, the technical scope of the present invention is not limited to the above-described embodiments. It is apparent to persons skilled in the art that various alterations or improvements can be added to the above-described embodiments. It is also apparent from the description of the claims that the form to which such alterations or improvements are made can be included in the technical scope of the present invention.

It should be noted that the operations, procedures, steps, stages, and the like of each process performed by an apparatus, system, program, and method shown in the claims, the specification, or the drawings can be realized in any order as long as the order is not indicated by "prior to," "before," or the like and as long as the output from a previous process is not used in a later process. Even if the operation flow is described by using phrases such as "first" or "next" for the sake of convenience in the claims, specification, and drawings, it does not necessarily mean that the process must be performed in this order.

EXPLANATION OF REFERENCES

10 Unmanned Aerial Vehicle (UAV);
20 UAV body;
30 image capturing apparatus;
32 memory;
36: communication interface;
40 propelling unit;
41 GPS receiver;
42 inertial measurement apparatus;
43 magnetic compass;
44 pressure altimeter;
45 temperature sensor;
46 humidity sensor;
50 gimbal;
60 image capturing apparatus;
70 gas sensor;
72 intake;
80 anemometer;
100 control unit;
200 pipeline;
300 remote operation apparatus;
301 transmitter;
310 control unit;
312 movement control unit;
314 acquisition unit;
316 detection unit;
318 reception unit;
320 calibration unit;
322 abnormality detection unit;
324 correction unit;
326 distribution generation unit;
330 memory;
340: communication interface;
1200: computer;
1210: host controller;
1212 CPU;
1214 RAM;
1220: input/output controller;
1222: communication interface; and
1230 ROM.

What is claimed is:

1. A gas leakage detection apparatus, comprising:

a movement control unit that controls a movement of a moving object on which a gas sensor is mounted;

an acquisition unit that acquires a measurement result of a target gas that is obtained by a measurement by the gas sensor while the moving object is moving over a target area and a response time from a start of the measurement until an output of the measurement result by the gas sensor; and a detection unit that detects a leakage of the target gas in the target area based on the measurement result and the response time, to identify a gas leakage spot, wherein the gas leakage detection apparatus is further configured to operate according to one of operation (a) and operation (b), wherein operation (a) comprises:

when a gas leakage candidate area exists in which the measurement result that is obtained by the measurement by the gas sensor, while the moving object is moving at a first velocity, satisfies a first condition, the movement control unit controls the movement of the moving object such that the moving object moves over the gas leakage candidate area at a second velocity that differs from the first velocity or the moving object stops in the gas leakage candidate area;

the acquisition unit acquires an additional measurement result of the target gas that is obtained by the measurement of the gas sensor while the moving object is moving at the second velocity over the gas leakage candidate area or stopped in the gas leakage candidate area; and when the additional measurement result satisfies a second condition, the detection unit identifies that the gas leakage candidate area is the gas leakage spot, wherein operation (b) comprises:

when a gas leakage candidate area exists in which the measurement result that is obtained by the measurement by the gas sensor, while the moving object is moving at a first altitude, satisfies a first condition, the movement control unit controls the movement of the moving object such that the moving object moves over the gas leakage candidate area at a second altitude that differs from the first altitude or the moving object stops at the gas leakage candidate area;

the acquisition unit acquires an additional measurement result of the target gas that is obtained by the measurement of the gas sensor while the moving object is moving at the second altitude over the gas leakage candidate area or stopped in the gas leakage candidate area; and when the additional measurement result satisfies a second condition, the detection unit identifies that the gas leakage candidate area is the gas leakage spot.

2. The gas leakage detection apparatus according to claim 1, wherein the acquisition unit further acquires location information of the moving object when the measurement result is acquired from the gas sensor; and the detection unit identifies a gas leakage spot at which a leakage of the target gas is detected in the target area further based on the location information.

3. The gas leakage detection apparatus according to claim 1, wherein the acquisition unit further acquires speed information of the moving object when the measurement result is acquired from the gas sensor; and the detection unit identifies the gas leakage spot further based on the speed information.

4. The gas leakage detection apparatus according to claim 1, wherein the movement control unit controls the movement of the moving object such that the moving object moves over the target area for multiple times; and the detection unit detects a leakage of the target gas for each area based on a gas concentration of the target gas based on the measurement result of each area in the target area.

5. The gas leakage detection apparatus according to claim 1, wherein the detection unit detects a leakage of the target gas for each area based on an average value of the gas concentration of the target gas of each area based on the measurement result of each area in the target area.

6. The gas leakage detection apparatus according to claim 1, further comprising a reception unit that receives a spatial resolution of gas leakage detection, wherein the movement control unit controls the movement of the moving object such that the moving object moves at a speed based on the spatial resolution.

7. The gas leakage detection apparatus according to claim 1, wherein the acquisition unit further acquires a measurement result of a target gas that is obtained by the measurement by the gas sensor while the moving object is moving outside the target area, and the gas leakage detection apparatus further comprises:

a calibration unit that performs a calibration of the gas sensor based on the measurement result of an area outside the target area.

8. The gas leakage detection apparatus according to claim 1, further comprising a correction unit that corrects an error that is generated on the measurement result of the target gas that is obtained by the measurement by the gas sensor due to a noise generated by driving a drive source of the moving object with a correction amount depending on a speed of the moving object.

9. The gas leakage detection apparatus according to claim 1, wherein the moving object further has an anemometer mounted thereon, and the movement control unit controls, based on a measurement result of the anemometer, the movement of the moving object such that the moving object moves from a downwind direction toward an upwind direction over the target area.

10. A gas leakage detection system, comprising:

the gas leakage detection apparatus according to claim 1, and a moving object having a drive source that is controlled by the gas leakage detection apparatus, and the gas sensor.

11. The gas leakage detection system according to claim 10, wherein the gas sensor is provided on a top surface on a body of the moving object.

12. The gas leakage detection system according to claim 11, wherein an intake of the target gas of the gas sensor is provided on the top surface such that the intake faces a front side in a case in which the moving object moves forward.

13. The gas leakage detection system according to claim 11, wherein an intake of the target gas of the gas sensor is provided on the top surface such that the intake faces a top side in a case in which the moving object moves upward.

14. The gas leakage detection system according to claim 10, comprising a plurality of moving objects, each moving object being identical to the moving object; wherein the plurality of moving objects perform a measurement of a gas concentration of the target gas at the gas sensor while moving over at least one target area assigned from a plurality of target areas included in an entire target area, the gas leakage detection system comprises:

a distribution generation unit that generates gas distribution information of the target gas in the entire target area based on a measurement result of each of the target areas provided from the plurality of moving objects, and the distribution generation unit generates the gas distribution information by deriving a baseline correction distribution of a gas concentration such that a residual error between measurement result group of respective pieces of the target areas provided from respective pieces of the moving objects moving over the target area is minimized.

15. The gas leakage detection system according to claim 14, wherein each of the plurality of target areas has an overlapping area that overlaps with an adjacent target area, and the distribution generation unit generates the gas distribution information by deriving a gas concentration of the target gas of the overlapping area based on each measurement result provided from each of the moving objects moving over the overlapping area.

16. A gas leakage detection apparatus, comprising:

a movement control unit that controls a movement of a moving object on which a gas sensor is mounted;

an acquisition unit that acquires a measurement result of a target gas that is obtained by a measurement by the gas sensor while the moving object is moving over a target area and a response time from a start of the measurement until an output of the measurement result by the gas sensor; and a detection unit that detects a leakage of the target gas in the target area based on the measurement result and the response time, to identify a gas leakage spot, wherein the detection unit detects a leakage of the target gas based on a level of deviation of a gas concentration of the target gas based on the measurement result that is obtained by the measurement by the gas sensor while the moving object is moving, and the level of deviation is calculated by a degree of deviation from a statistical average of data of the gas concentration of the target gas.

17. A gas leakage detection method, comprising:

controlling a movement of a moving object on which a gas sensor is mounted;

acquiring a measurement result of a target gas that is obtained by a measurement by the gas sensor while the moving object is moving over a target area and a response time from a start of the measurement until an output of the measurement result by the gas sensor; and detecting a leakage of the target gas in the target area based on the measurement result and the response time, to identify a gas leakage spot, wherein the gas leakage detection method further comprises one of procedure (a) and procedure (b), wherein procedure (a) comprises:

when a gas leakage candidate area exists in which the measurement result that is obtained by the measurement by the gas sensor, while the moving object is moving at a first velocity, satisfies a first condition, controlling the movement of the moving object such that the moving object moves over the gas leakage candidate area at a second velocity that differs from the first velocity or the moving object stops in the gas leakage candidate area;

acquiring an additional measurement result of the target gas that is obtained by the measurement of the gas sensor while the moving object is moving at the second velocity over the gas leakage candidate area or stopped in the gas leakage candidate area; and when the additional measurement result satisfies a second condition, identifying that the gas leakage candidate area is the gas leakage spot, wherein procedure (b) comprises:

when a gas leakage candidate area exists in which the measurement result that is obtained by the measurement by the gas sensor, while the moving object is moving at a first altitude, satisfies a first condition, controlling the movement of the moving object such that the moving object moves over the gas leakage candidate area at a second altitude that differs from the first altitude or the moving object stops at the gas leakage candidate area;

acquiring an additional measurement result of the target gas that is obtained by the measurement of the gas sensor while the moving object is moving at the second altitude over the gas leakage candidate area or stopped in the gas leakage candidate area; and when the additional measurement result satisfies a second condition, identifying that the gas leakage candidate area is the gas leakage spot.

* * * * *